US00PP14396P29

(12) United States Plant Patent
Repp

(10) Patent No.: US PP14,396 P2
(45) Date of Patent: Dec. 23, 2003

(54) COLEUS PLANT NAMED 'SOUTH OF THE BORDER'

(50) Latin Name: *Coleus×hybrida*
Varietal Denomination: South of the Border

(76) Inventor: Ralph Repp, 423 County Rd., Waynesville, NC (US) 28785

( * ) Notice: Subject to any disclaimer, the term of this patent is extended or adjusted under 35 U.S.C. 154(b) by 0 days.

(21) Appl. No.: 10/291,020

(22) Filed: Nov. 8, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Annette Para
(74) *Attorney, Agent, or Firm*—C. A. Whealy

(57) ABSTRACT

A new and distinct cultivar of Coleus plant named 'South of the Border', characterized by its upright and mounded plant habit; pale yellow and green bi-colored leaves; and numerous small violet blue-colored flowers arranged on terminal verticillasters.

1 Drawing Sheet

Botanical classification/cultivar designation: Coleus×hybrida South of the Border.

BACKGROUND OF THE INVENTION

The present Invention relates to a new and distinct cultivar of Coleus plant, botanically known as *Solenostemon scutellarioides*, and hereinafter referred to by the cultivar name South of the Border.

The new cultivar was discovered by the Inventor in a controlled environment in Waynesville, N.C. as a naturally-occurring branch mutation of a the *Solenostemon scutellarioides* cultivar Aurora, not patented. The new Coleus was observed within a population of plants of the cultivar Aurora in July, 2000. This branch mutation was selected on the basis of its unique leaf coloration.

Asexual reproduction of the new cultivar by terminal cuttings taken in Waynesville, N.C. since July, 2000, has shown that the unique features of this new Coleus are stable and reproduced true to type in successive generations.

SUMMARY OF THE INVENTION

Plants of the cultivar South of the Border have not been observed under all possible environmental conditions. The phenotype may vary somewhat with variations in environment such as temperature and light intensity without, however, any variance in genotype.

The following traits have been repeatedly observed and are determined to be the unique characteristics of 'South of the Border'. These characteristics in combination distinguish 'South of the Border' as a new and distinct cultivar:

1. Upright and mounded plant habit.
2. Pale yellow and green bi-colored leaves.
3. Numerous small violet blue-colored flowers arranged on terminal verticillasters.

Plants of the new Coleus are most similar to plants of the parent, the cultivar Aurora. Plants of the new Coleus differ from plants of the parent selection primarily in foliage color as plants of the cultivar Aurora have upper and lower leaf surfaces strongly flushed with red purple and red purple-colored venation.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Coleus.

The photograph at the top of the sheet comprises a side perspective view of typical plant of 'South of the Border' grown in a container.

The photograph at the bottom of the sheet comprises a close-up view of typical leaves and a typical inflorescence of 'South of the Border'.

DETAILED BOTANICAL DESCRIPTION

The cultivar South of the Border has not been observed under all possible environmental conditions. The phenotype may vary somewhat with variations in environment such as temperature and light intensity without, however, any variance in genotype.

The aforementioned photographs, following observations and measurements describe plants grown during the winter and spring in Encinitas, Calif., in an outdoor nursery and under conditions which approximate commercial production cultural and environmental conditions. Plants were about 14 weeks from cuttings and were grown in one-gallon containers. During the production of the plants, day temperatures averaged 24° C. and night temperatures averaged 19° C.

In the following description, color references are made to The Royal Horticultural Society Colour Chart, 1995 Edition, except where general terms of ordinary dictionary significance are used.

Botanical classification: *Solenostemon scutellarioides* cultivar South of the Border.

Parentage: Naturally-occurring branch mutation of the *Solenostemon scutellarioides* cultivar Aurora, not patented.

Propagation:

*Type cutting.*—Terminal cuttings.

*Time to initiate roots.*—Summer: About 7 days at 20° C. Winter: About 9 days at 20° C.

*Time to develop roots.*—Summer: About 18 days at 20° C. Winter: About 20 days at 20° C.

*Root description.*—Fine, fibrous, white in color.

*Rooting habit.*—Freely branching.

Plant description:

*Form.*—Annual flowering plant; upright and mounded. Moderate to rapid growth rate.

*Plant height.*—About 56 cm.

*Plant diameter.*—About 70 cm.

*Branching habit.*—Freely branching with potentially two lateral branches forming at every node.

*Lateral branches.*—Length: About 55 cm. Diameter: About 1.2 cm. Internode length: About 2 cm. Shape, in cross-section: Squarish. Texture: Glabrous. Color: 46B to 46D.

*Foliage description.*—Arrangement: Opposite; simple. Length: About 8.5 cm. Width: About 6.5 cm. Shape: Elliptic. Apex: Broadly acute. Base: Attenuate to obtuse. Margin: Crenate, scalloped; ruffled. Texture, upper and lower surfaces: Glabrous. Venation pattern: Pinnate. Color: Young foliage, upper surface: Center, 10B to 10C; towards the margins, 146A. Young foliage, lower surface: Center, 10C; towards the margins, 146B; towards base, flushed with 65B. Fully expanded foliage, upper surface: Center, 11D; towards the margins, 144A. Fully expanded foliage, lower surface: Center, 11D; towards the margins, 147C. Venation, upper and lower surfaces: 11D. Petiole length: About 3.5 mm. Petiole diameter: About 2.5 mm. Petiole color: 2C.

Flower description:

*Flower type and habit.*—Numerous single bilabiate flowers arranged in verticillasters arranged on terminal elongated spikes. Verticillasters with 10 to 12 verticels. Individual flowers face mostly outward. Freely flowering with about 12 flowers per verticel. Flowers not persistent.

*Natural flowering season.*—Plants typically flower during the spring; flowering continuous during this period.

*Flower longevity on the plant.*—About three to four days.

*Fragrance.*—Faint; sweet, violet-like.

*Spike length.*—About 9 cm.

*Spike diameter.*—About 2 cm.

*Flowers.*—Appearance: Zygomorphic; bilabiate. Diameter: About 6 mm by 3 mm. Depth (height): About 9 mm.

*Flower buds (showing color).*—Length: About 4 mm. Diameter: About 2.5 mm. Shape: Ovoid. Color: 144D; towards the apex, 90C.

*Corolla.*—Petal arrangement/appearance: Bilabiate; five petals, upper two petals fused into a banner and lower three petals fused into a horizontal keel, all five petals fused at base into a tubular structure. Length, banner: About 2 mm. Length, keel: About 6 mm. Width, banner: About 2 mm. Width, keel: About 3 mm. Apex, banner: Rounded to crenate. Apex, keel: Acute, pointed. Margin, banner and keel: Entire. Texture, banner and keel: Smooth. Color, banner and keel: When opening, upper surface: 92A to 92B. When opening, lower surface: 92A to 92C. Fully opened, upper surface: 92A to 92B, color becoming closer to 92B to 92C with development; towards the base, 155D. Fully opened, lower surface: 155D, towards the apex, 92B to 92C.

*Calyx.*—Quantity/arrangement: One single calyx tube per flower; five fused sepals. Length: About 3 mm. Diameter: About 2 mm. Apex: Acuminate. Texture, upper and lower surfaces: Slightly pubescent. Color, immature and mature, upper and lower surfaces: 144B.

*Peduncles.*—Length: About 1.2 cm. Diameter: About 2.5 mm. Strength: Strong. Angle: Upright. Color: 144D.

*Pedicels.*—Length: About 2.5 mm. Diameter: Less than 1 mm. Strength: Moderately strong. Angle: Horizontal. Color: 144D.

*Reproductive organs.*—Stamens: Quantity per flower: Four. Stamen length: Less than 1 mm. Anther shape: Oval. Anther length: Less than 1 mm. Anther color: Close to 90C. Pollen amount: Scarce. Pollen color: Close to 155A. Pistils: Quantity per flower: One. Pistil length: About 7 mm. Style length: About 6 mm. Style color: 92D. Stigma shape: Rounded. Stigma color: 92C. Ovary color: 144C.

*Seed/fruit.*—Seed nor fruit production has not been observed.

Disease/pest resistance: Plants of the new Coleus have not been noted to be resistant to pathogens or pests common to Coleus.

Temperature tolerance: Plants of the new Coleus have been observed to tolerate temperatures from 2 to 35° C.

It is claimed:

1. A new and distinct cultivar of Coleus plant named 'South of the Border', as illustrated and described.

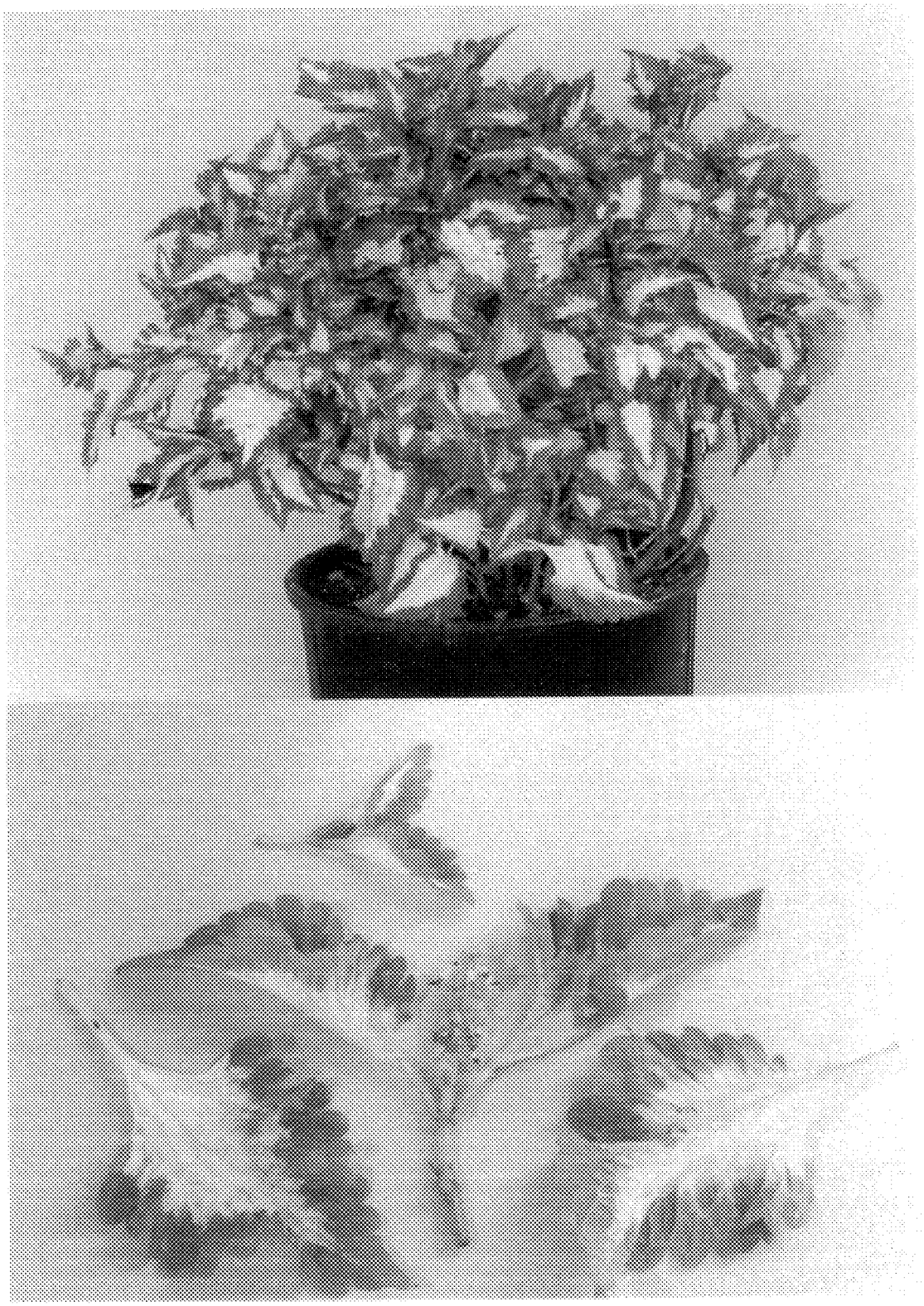

* * * * *